United States Patent [19]

Jahn

[11] Patent Number: 5,047,053
[45] Date of Patent: Sep. 10, 1991

[54] PERMANENT MIDDLE EAR VENT TUBE AND METHOD OF INSERTION

[75] Inventor: Anthony F. Jahn, Tenafly, N.J.
[73] Assignee: Smith & Nephew Richards Inc., Memphis, Tenn.
[21] Appl. No.: 485,642
[22] Filed: Feb. 27, 1990
[51] Int. Cl.⁵ .............................................. A61F 2/18
[52] U.S. Cl. ...................................................... 623/10
[58] Field of Search ........................ 623/10, 11, 16, 66

[56] References Cited

U.S. PATENT DOCUMENTS

| | | | |
|---|---|---|---|
| 3,982,545 | 9/1976 | Silverstein | 623/10 |
| 4,094,303 | 6/1978 | Johnston | 623/10 |
| 4,676,796 | 6/1987 | Merwin et al. | 623/10 |
| 4,744,792 | 5/1988 | Sander et al. | 623/10 |

FOREIGN PATENT DOCUMENTS

| | | | |
|---|---|---|---|
| 2627079 | 8/1989 | France | 623/10 |
| 2041759 | 9/1980 | United Kingdom | 623/10 |

OTHER PUBLICATIONS

William M. Luxford, et al., Ventilation Tubes: Indications and Complications, Oct. 1984.
Mark T. Weigel, MD, et al., A Prospective Randomized Study of Four Commonly Used Tympanotomy Tubes, Jan. 16, 1988.
"Vitalluum Surgical Appliances", Austenal Laboratories, Inc. (Catalog) Surgical Div., New York, N.Y., Mar. 1948, p. 20.

Primary Examiner—David J. Isabella
Attorney, Agent, or Firm—Pravel, Gambrell, Hewitt, Kimball & Krieger

[57] ABSTRACT

A permanent middle ear vent tube and method for permanent ventilation of the middle ear include implanting a tube with a tubular base portion have at one end an eccentric flange and formed of a non-compressible material. The tube is implanted in a notch drilled into the bony canal wall and rotating the tube into place.

12 Claims, 2 Drawing Sheets

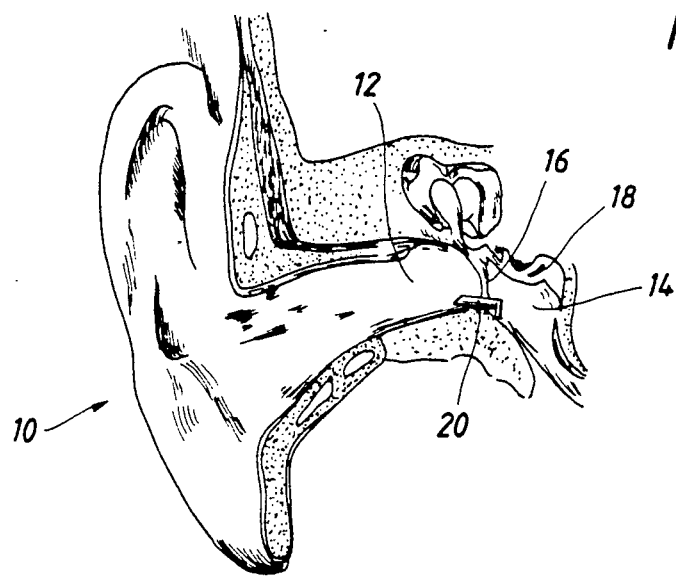
FIG. 1
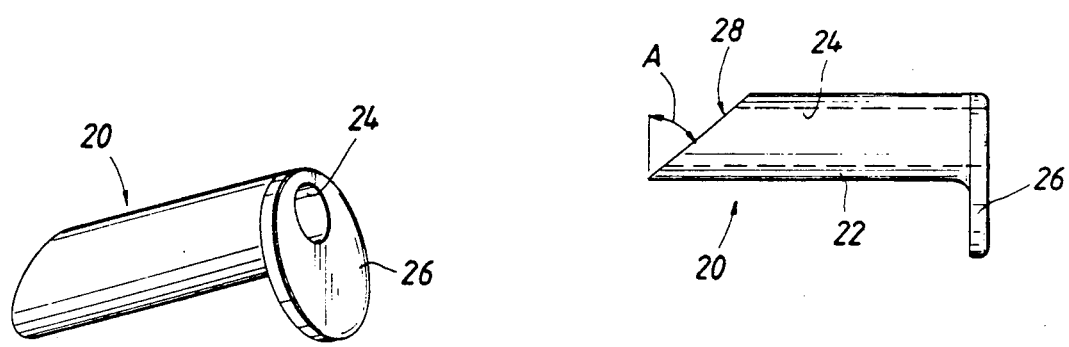
FIG. 2
FIG. 3
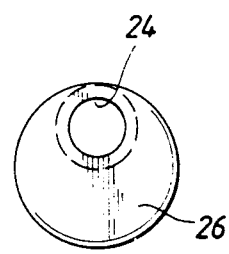
FIG. 4
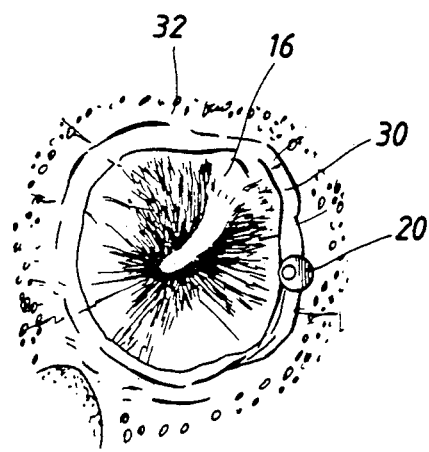
FIG. 5

PERMANENT MIDDLE EAR VENT TUBE AND METHOD OF INSERTION

THE FIELD OF THE INVENTION

The present invention relates to an apparatus and method for permanent ventilation of the middle ear.

BACKGROUND OF THE INVENTION

Successful treatment of persistent serous otitis media, adhesive otitis media and certain types of chronic suppurative otitis media requires some means of permanently aerating the middle ear. There are known procedures for inserting ventilation tubes through the tympanic membrane to equalize pressure and drain fluids from the middle ear.

Insertion of ventilation tubes through the tympanic membrane has disadvantages because tissue growth and other factors cause movement and eventual extrusion of the tube from the tympanic membrane. Extrusion of a ventilation tube enhances the risk of perforation of the tympanic membrane which can require surgery to repair and could result in the formation of scar tissue on the tympanic membrane.

Ventilation tubes have been designed for longer retention in the tympanic membrane. These tubes generally have enlarged flanges and are formed of compressible materials such as silicon rubber. In such tubes, the flanges are compressed for insertion through an incision in the tympanic membrane and released in the middle ear cavity. These large flanges operate to anchor the ventilation tube and inhibit easy extrusion. While large-flanged ventilation tubes may be retained for a longer period of time, they suffer from the same extrusion and perforation problems discussed above and generally are extruded within three to four years after insertion.

The compressible materials used such as the silicone rubbers are not suitable for permanent implantation. The materials have been described as having a "tacky" surface, which is somewhat porous and causes retention of fluid on the implant, impeding drainage and increasing risk of infection. More suitable biocompatible materials are not useful in these large-flanged implants because of their rigid structure.

U.S. Pat. No. 3,982,545 to Silverstein, describes another type of ventilation tube deemed to be permanent, which is inserted through a specific region of the bony external ear canal. Although this tube is designed to be permanent, it also has problems. As described in the Silverstein patent, the tube is installed by the relatively complicated surgical procedure of first exposing the middle ear structure by cutting a flap in the tympanic membrane to determine whether the patent's facial recess and bony overhang are adequate for the procedure. This procedure opens the tympanic membrane and requires drainage of the middle ear during the procedure. This procedure also requires drilling through the facial ridge or alternatively through the mastoid air cells, with the concomitant risk of damage to the facial nerve. The Silverstein implant is also formed of a compressible material such as silicone to facilitate its insertion and retention in the drilled canal, which has the problems discussed above.

SUMMARY OF THE INVENTION

The present invention provides a method and apparatus for permanent ventilation of the middle ear, which solves the problems discussed above. The ventilation tube of the present invention is formed of a biocompatible material which is either porous or dense and preferably non-compressible.

The ventilation tube of the present invention includes a tubal base portion with an eccentric flange at the proximal end of the base portion for insertion and permanent retention in the middle ear cavity. The distal end can be beveled on the side opposite the flange to facilitate drainage.

The tube is installed by separating the fibrous annulus of the tympanic membrane from the bony canal wall and forming a groove in the bone of the external canal. The ventilation tube is then inserted into the drilled canal. The implant is then rotated and pushed to rest the length of the tubular base portion in the groove in the bone of the external canal. In its final position, the flange of the implant rests along the vertical wall of the middle ear chamber while the opposite end of the tubular base portion projects into the outer ear cavity.

BRIEF DESCRIPTION OF THE INVENTION

A better understanding of the invention can be obtained from the detailed description of a preferred embodiment set forth below, considered in conjunction with the appended drawings, in which:

FIG. 1 is a perspective view of an ear showing in particular in cross section the outer and middle ear cavity separated by a tympanic membrane under which a tube of the present invention has been implanted;

FIG. 2 is a perspective view of a tube of the present invention;

FIG. 3 is a front plan view of the tube of FIG. 2;

FIG. 4 is an end plan view of the tube of FIG. 2;

FIG. 5 is a schematic view of the tympanic membrane in which a tube of the present invention has been implanted.

DETAILED DESCRIPTION OF A DETAILED EMBODIMENT

Figure 6:
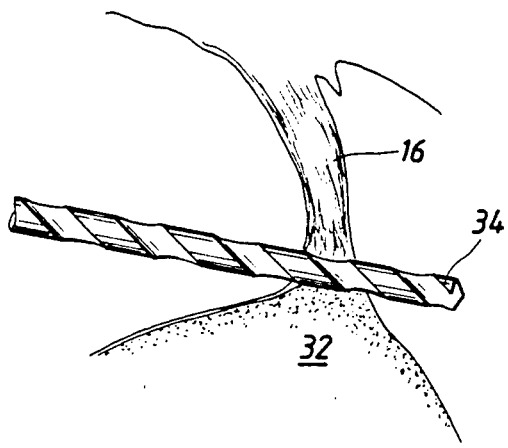
FIGS. 6-9 are sectional views of a tympanic membrane showing a procedure for implanting a tube of the present invention.

Referring in particular to FIG. 1, the tube and method of the present invention will be described in detail. FIG. 1 illustrates a typical ear 10 which includes an outer ear cavity 12 and a middle ear cavity 14 separated by a tympanic membrane 16. Vibrations caused by sound waves impinging on the tympanic membrane 16 are transmitted in the form of vibrations through a chain of three movable bones known as ossicles 18 to the internal ear (not shown).

A ventilation tube 20 of the present invention is shown inserted under the tympanic membrane 16 in order to provide communication between the outer and middle ear cavities 12, 14, respectively, for the reasons discussed above. The method of insertion is described in greater detail below.

The tube 20, shown in detail in FIGS. 2-4, includes an elongated tubular base portion 22 with an opening or lumen 24 extending throughout the length of the base portion 22. A flange 26 is formed at the proximal end of the base portion 22. As shown best in FIG. 3, the flange 26 is circular in shape and flush against one side of the tubular member 22.

The flange 26 extends perpendicularly away from the opposite side of the tubular member 22 so that the outer wall of the base portion member 22, see FIG. 4, is tangential to the outer edge of the circular flange 26. This structure of the tube with what is called an eccentric flange allows the tube to be inserted easily into an opening formed in the tympanic membrane through a "buttoning" process as described below. The distal end of the tube 22 is preferably beveled at an angle A greater than 20°, preferably about 45°. This beveled surface 28 is opposite the extended end of the flange 26 so that as shown in FIG. 1, the beveled end faces away from the wall that defines the outer ear canal 12 to allow ventilation between the middle ear cavity 14 and outer ear cavity 12.

The ventilation tube 20 is formed of a non-compressible material which must be biocompatible. The material can be formed with a porous outer surface or one which encourages surface adhesion of surrounding material. An example of suitable known materials with a porous outer surface to encourage tissue ingrowth are porous ultra-high molecular weight polyethylene. Other known biocompatible materials designed to allow for surface adhesion of surrounding tissue are dense hydroxylapatite which encourages osteointegration or surface adhesion of surrounding tissue to the outer surface of the tube 20. Another suitable material is titanium with a matte surface formed by chemical etching which has also been found to provide suitable surface adhesion of surrounding tissue.

As shown in FIG. 5, the tube 20 is implanted at the outer perimeter of the tympanic membrane 16 under a fibrous ring 30 which connects the tympanic membrane 16 to surrounding bone 32. An advantage of the tube and method of the present invention is that the tube 20 can be implanted at any desired point around the periphery of the tympanic membrane 16.

As shown in FIGS. 6–9, the method of implanting the tube 20 includes drilling an notch with a suitable microsurgical drill bit 34 into the bony annulus of the tympanic membrane ring 30 preferably forming a small notch in the surrounding bone 32.

Figure 7:
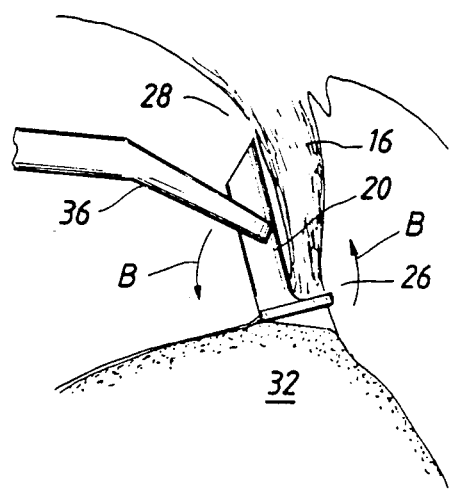

As shown in FIG. 7, the beveled or distal end 28 of the tube 20 is grasped by a pair of standard microsurgical forceps 36 so that the eccentric flange 26 is inserted through the opening formed in the bony annulus 32. After the flange 26 is inserted in the position shown in FIG. 7, the tube is moved so that it rests in the preformed notch of the bony annulus.

Figure 8:
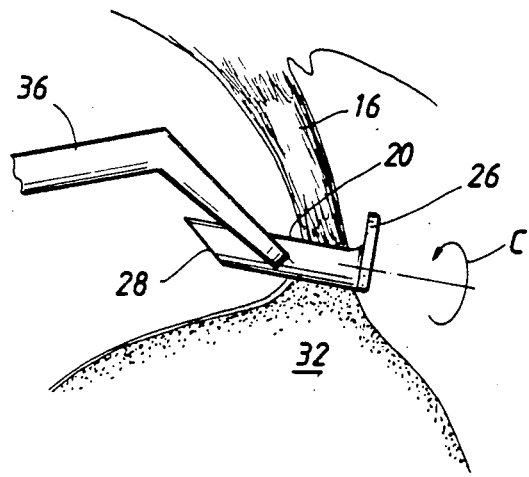
Figure 9:
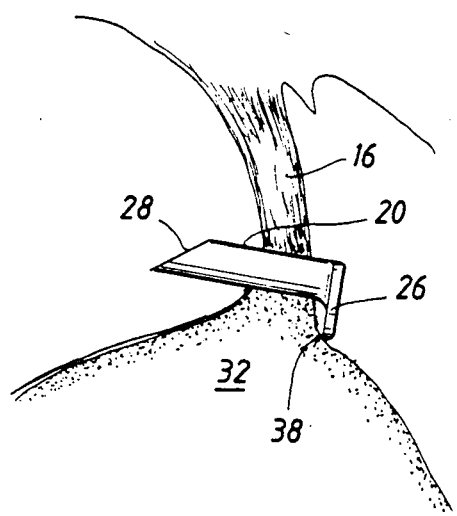

When the tube 20 is in the position shown in FIG. 8, the flange 26 is facing toward the tympanic membrane and the beveled distal end 28 is facing the surrounding bone 32, which are opposite the way the tube should be oriented. In order to position the tube 20 properly, the forceps 36 are manipulated to rotate the tube 20 in the direction of an arrow C shown in FIG. 8 to the position shown in FIG. 9 where the flange rests adjacent to a ridge 38 located in the middle ear cavity which tends to hold the tube 20 in place and prevents it from extruding out of the tympanic membrane 16. In this position, the distal end is facing upwardly so that free ventilation from the middle ear cavity 14 to the outer ear cavity 12 is not impeded.

By providing the tube of the design described above, a permanent implantation can be made which will remain in place indefinitely. With the tube being formed with an eccentric flange, the tube can easily be buttonholed in place a described and then rotated so that the flange rests against a naturally occurring ridge to prevent it from being extruded from the ear. This implantation method is desirable because the tube is formed of a non-compressible material. By beveling the distal end of the tube, the cross sectional area is increased for better ventilation and decreased likelihood of clogging.

The foregoing description is considered to be illustrative and not limiting and variations and improvements to the invention can be made without departing from the spirit and scope of the invention. All such variations and improvements are contemplated as falling within the scope of the appended claims in which:

I claim:

1. A permanent ear ventilation tube adapted to provide ventilation between the middle ear and the outer ear, comprising:

an elongated base portion and a flange formed of a non-compressible and biocompatible material;

said elongated base portion terminating at opposite ends and having a longitudinal opening extending therebetween;

said flange eccentrically connected at one end of said elongated base portion wherein the ventilation tube, in its implanted position, has the flange resting on the surface defining the middle ear cavity and the elongated base portion extending into the outer ear cavity.

2. The tube of claim 1 wherein the base portion is tubular in shape.

3. The tube of claim 1, wherein the flange is circular in shape and oriented perpendicular to the base portion.

4. The tube of claim 1, wherein the end of the base portion opposite the flange is formed with a bevel facing away from the side of the base member from which the flange projects.

5. The tube of claim 4, wherein the bevel is greater than 20°.

6. The tube of claim 5, wherein the bevel is about 45°.

7. The tube of claim 1, wherein at least the outer surface of the base member and flange are formed with pores to accommodate tissue ingrowth.

8. The tube of claim 1, wherein at least the outer surface of the base member and flange are formed to encourage tissue adherence.

9. The tube of claim 8, wherein base member and flange are formed of dense hydroxylapetite.

10. The tube of claim 8, wherein the base member and flange are formed of titanium with the outer surface chemically treated to form a surface which encourages tissue adherence.

11. A method of implanting permanent ear ventilation tube, comprising the steps of:

forming a notch under the fibrous ring of the tympanic membrane portion of an ear at the interface of the fibrous and the bony canal wall;

inserting a ventilation tube formed of an elongated base, portion with a longitudinal opening and a flange eccentrically connected to one end of the base portion and projecting outwardly from one side of the base portion, the longitudinal opening extending through the flange and the base portion and flange being formed of a non-compressible, biocompatible material;

inserting the flange of said tube into the middle ear cavity and rotating the tube so that the flange will face the surface defining the middle ear cavity.

12. The method of claim 11, wherein the distal end of the tube is formed with a beveled surface on the end of the tube opposite the flange, the beveled surface facing away from the surface defining the outer ear cavity after the step of rotating.

* * * * *